US011447748B2

(12) United States Patent
Katz et al.

(10) Patent No.: US 11,447,748 B2
(45) Date of Patent: *Sep. 20, 2022

(54) ENCAPSULATED ADIPOSE-DERIVED STEM CELLS, METHODS FOR PREPARATION AND THERAPUTIC USE

(71) Applicant: JoinTechLabs, Inc., North Barrington, IL (US)

(72) Inventors: Nathan Katz, North Barrington, IL (US); Felix Pustilnik, Walnut Creek, CA (US)

(73) Assignee: JointTechLabs, Inc., North Barrington, IL (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/993,503

(22) Filed: Aug. 14, 2020

(65) Prior Publication Data

US 2020/0370017 A1 Nov. 26, 2020

Related U.S. Application Data

(60) Continuation of application No. 15/947,297, filed on Apr. 6, 2018, now Pat. No. 10,745,666, which is a division of application No. 13/193,468, filed on Jul. 28, 2011, now Pat. No. 9,938,501.

(60) Provisional application No. 61/368,513, filed on Jul. 28, 2010, provisional application No. 61/368,528, filed on Jul. 28, 2010.

(51) Int. Cl.
| | |
|---|---|
| *A61K 9/00* | (2006.01) |
| *A61K 9/16* | (2006.01) |
| *A61K 35/28* | (2015.01) |
| *C12N 5/077* | (2010.01) |
| *C12N 5/0775* | (2010.01) |
| *A61L 27/38* | (2006.01) |
| *A61L 27/52* | (2006.01) |
| *A61K 35/12* | (2015.01) |

(52) U.S. Cl.
CPC .......... *C12N 5/0655* (2013.01); *A61K 9/0019* (2013.01); *A61K 9/1658* (2013.01); *A61K 35/28* (2013.01); *A61L 27/3834* (2013.01); *A61L 27/52* (2013.01); *C12N 5/0667* (2013.01); *A61K 2035/126* (2013.01); *C12N 2533/56* (2013.01)

(58) Field of Classification Search
None
See application file for complete search history.

(56) References Cited

U.S. PATENT DOCUMENTS

| 5,486,359 | A | 1/1996 | Caplan |
| 6,150,505 | A | 11/2000 | Marx |
| 10,745,666 | B2* | 8/2020 | Katz .................. A61L 27/3834 |
| 2002/0110544 | A1 | 8/2002 | Goldberg |
| 2002/0155096 | A1 | 10/2002 | Chancellor |
| 2003/0012734 | A1 | 1/2003 | Pathak |
| 2003/0211083 | A1 | 11/2003 | Vogel |
| 2004/0157951 | A1 | 8/2004 | Wolf |
| 2005/0260175 | A1 | 11/2005 | Wulur |
| 2006/0233854 | A1 | 10/2006 | Seliktar |
| 2008/0031858 | A1 | 2/2008 | Chan |
| 2008/0044900 | A1 | 2/2008 | Mooney |
| 2009/0269406 | A1 | 10/2009 | Panitch |
| 2010/0003328 | A1 | 1/2010 | Yasuda |
| 2012/0087983 | A1 | 4/2012 | Katz |
| 2013/0039990 | A1 | 2/2013 | Xu |

OTHER PUBLICATIONS

Altman, Roy D., MD, "Osteoarthritis (OA)", Merck Sharp & Dohme Corp., Merck Manual Home Health Edition, Feb. 2008, pp. 1-5, cited from the Office Action dated Apr. 10, 2014, from U.S. Appl. No. 13/245,639.

Gurevich, "Fibrin Microbeads for Isolating and Growing Bone Marrow-Derived Progenitor Cells Capable of FormingBone Tissue", Tissue Engineering, vol. 8, No. 4, pp. 661-672, 2002.

Non-Final Office Action dated Apr. 10, 2014, received from the U.S. Patent and Trademark Office, for U.S. Appl. No. 13/245,639, pp. 1-13.

* cited by examiner

*Primary Examiner* — Robert T. Crow
*Assistant Examiner* — John P Nguyen
(74) *Attorney, Agent, or Firm* — Lempia Summerfield Katz LLC

(57) ABSTRACT

A therapeutic composition comprising a purified fraction of adipose-derived mesenchymal stem cells encapsulated in a three-dimensional biocompatible gel matrix, and methods, and systems for preparing and using encapsulated adipose-derived mesenchymal stem cells. Hydrogel microbeads encapsulating stem cells maintain the viability and location of the stem cells for an extended period as compared to stem cells in suspension. The gel matrix allows the release of cellular factors from the encapsulated stem cells to surrounding tissues to achieve desired therapeutic results.

15 Claims, No Drawings

ENCAPSULATED ADIPOSE-DERIVED STEM CELLS, METHODS FOR PREPARATION AND THERAPUTIC USE

CLAIM OF PRIORITY

This application is a continuation of U.S. application Ser. No. 15/947,297 (now U.S. Pat. No. 10,745,666), which is a divisional of U.S. application Ser. No. 13/193,468 (now U.S. Pat. No. 9,938,501), which claims priority to U.S. Provisional Application No. 61/368,513 filed on Jul. 28, 2010 and to U.S. Provisional Application No. 61/368,528, each of U.S. application Ser. No. 15/947,297 (now U.S. Pat. No. 10,745,666), US Application No. 13/193,468 (now U.S. Pat. No. 9,938,501), U.S. Provisional Application No. 61/368,513, and U.S. Provisional Application No. 61/368,528 are incorporated herein by reference in their entirety.

FIELD OF THE INVENTION

This invention relates generally to therapeutic compositions including stem cells derived from adipose tissue, including systems for preparing, delivering and utilizing such therapeutic compositions.

BACKGROUND OF THE INVENTION

Regenerative medicine can be defined as harnessing the body's regenerative mechanisms in a clinically targeted manner, using them in ways that are not part of the normal healing mechanism or by artificially amplifying normal mechanisms. Stem cells are pluripotent or multipotent cells with the potential to differentiate into a variety of other cell types, which perform one or more specific functions and have the ability to self-renew. It has been found that stem cells from a variety of sources can be used for multiple therapeutic or prophylactic purposes. For example, hematopoetic stem cells (HSCs) derived from bone marrow are multipotent stem cells that can give rise to cell types from the myeloid (monocytes and macrophages, neutrophils, basophils, eosinophils, erythrocytes, megakaryocytes/platelets, dendritic cells), and lymphoid lineages (T-cells, B-cells, NK-cells). Mesenchymal stem cells ("MSCs") derived from multiple tissues in the adult body are multipotent non-hematopoietic stem cells and are characterized by extensive proliferative ability in an uncommitted state while retaining the potential to give rise to cell types including osteoblasts, myocytes, chondrocytes, adipocytes, endothelial cells and beta pancreatic islet cells. MSCs are present in which arise from the embryonic mesoderm (e.g., hematopoietic cells and connective tissue). Thus, stem cells can be isolated from many tissue sources within the adult body.

Adipose tissue refers to fat including the connective tissue that stores the fat. Adipose tissue includes stem cells and endothelial precursor cells. As used herein, "adipose tissue" refers to a tissue containing multiple cell types including adipocytes and microvascular cells. It has been discovered that adipose tissue is an especially rich and practical source of mesenchymal stem cells. This finding is due, at least in part, to the ease of harvesting adipose tissue and the ease of removing the major non-stem cell component of adipose tissue, the adipocyte. In fact, a large quantity of mesenchymal stem cells can be obtained by simple aspiration from adipose tissue, for example, from lipoaspirate samples from aesthetic interventions. The lipoaspirate is typically centrifuged to separate the active cellular component from the mature adipocytes and connective tissue. The pellet containing the active cellular component (e.g., the component containing adipose-derived stem cells) is referred to as processed lipoaspirate (PLA).

Adipose-derived stem cells (ADSCs), methods for extracting such cells and methods for using such cells are disclosed for example in: Gimble et al., "Adipose-derived Stem Cells for Regenerative Medicine" Circ. Res. 100:1249-1260 (2007); Utsonomiya et al., "Human Adipose-Derived Stem Cells: Potential Clinical Applications in Surgery" Surg Today 41:18-23 (2011); Casteilla et al., "Adipose-derived stromal cells: Their identity and uses in clinical trials, an update" World J Stem Cells 3(4):25-33 (2011); U.S. Pat. No. 6,777,231 entitled "Adipose-Derived Stem Cells and Lattices" to Katz et al.; U.S. Pat. No. 7,901,672 entitled "Methods Of Making Enhanced Autologous Fat Grafts" to Fraser et al.; U.S. Patent Publication 2009/0304644 entitled "Systems And Methods For Manipulation Of Regenerative Cells Separated And Concentrated From Adipose Tissue" to Hedrick et al.; and U.S. Pat. No. 7,390,484 entitled "Self-Contained Adipose Derived Stem Cell Processing Unit" to Fraser et al., all of which are incorporated herein by reference.

SUMMARY OF THE INVENTION

Adipose-derived stem cells may be used for therapeutic and cosmetic applications. Among other things, the cells may be used for regenerative medicine, such as diseases that can be treated with regenerating cells. The present invention relates generally to therapeutic compositions including adipose-derived stem cells derived from adipose tissue, as well as systems for preparing, delivering and utilizing such therapeutic compositions. The adipose-derived stem cells may be administered to a patient as part of a therapeutic composition as described herein. In a preferred embodiment, the adipose-derived stem cells are provided in a three-dimensional platform. The three-dimensional platform includes adipose-derived stem cells encapsulated in a biocompatible hydrogel and formed into microbeads which protect and support the stem cells when introduced to the human body thereby enhancing therapeutic efficacy of the treatment as compared to stem cells in suspension These and other objects, features and advantages of the invention will be apparent from the detailed description which follows.

DETAILED DESCRIPTION OF THE PREFERRED EMBODIMENTS

Reference will now be made in detail to the presently preferred embodiments of the invention. Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be practiced in conjunction with various cell or tissue separation techniques that are conventionally used in the art, and only so much of the commonly practiced process steps are included herein as are necessary to provide an understanding of the present invention.

Extraction and Isolation of Stem Cells

The present disclosure provides for the isolation and utilization of stem cells. Such cells can be isolated from almost any embryonic or adult tissue including, but not limited to endothelial tissue from umbilical cord vein, endothelial tissue from foreskin, endometrial tissue, human embryonic stem cells, and adipose tissue. Pluripotent cells can also be artificially produced by inducing pluripotency such as described in Takahashi, K. & Yamanaka, S. Cell; 126: 663-676 (2006).

Mesenchymal Stem Cells (MSCs) are stem cells that can differentiate readily into lineages including osteoblasts, myocytes, chondrocytes, adipocytes, endothelial cells and beta pancreatic islet cells (Pittenger, et al., Science, Vol. 284, pg. 143 (1999); Haynesworth, et al., Bone, Vol. 13, pg. 69 (1992); Prockop, Science, Vol. 276, pg. 71 (1997)). MSCs, also known in the literature as bone marrow stem cells, skeletal stem cells, and multipotent mesenchymal stromal cells, are non-hematopoietic progenitor cells isolated from adult tissues, and are characterized in vitro by their extensive proliferative ability in an uncommitted state while retaining the potential to differentiate along various lineages of mesenchymal origin, including chondrocyte, osteoblast, and adipocyte lineages, in response to appropriate stimuli. In vitro studies have demonstrated the capability of MSCs to differentiate into muscle (Wakitani, et al., Muscle Nerve, Vol. 18, pg. 1417 (1995)), neuronal-like precursors (Woodbury, et al., J. Neurosci. Res., Vol. 69, pg. 908 (2002); Sanchez-Ramos, et al., Exp. Neurol., Vol. 171, pg. 109 (2001)), cardiomyocytes (Toma, et al., Circulation, Vol. 105, pg. 93 (2002); Fakuda, Artif. Organs, Vol. 25, pg. 187 (2001)) and possibly other cell types. MSCs are present in multiple tissues in the body which arise from the embryonic mesoderm (e.g., hematopoietic cells and connective tissue). As such, pluripotent cells useful for the present invention can be isolated from any of these tissue sources and can be induced to differentiate into any of these cell types.

In general, pluripotent cells are obtained from non-pathological post-natal mammalian adipose tissues. Pluripotent cells can be obtained from a source of adipose tissue, such as the stromal fraction of adipose tissue. The pluripotent cells can be obtained from any suitable source of adipose tissue from any suitable animal, including humans, having adipose tissue. For example, adipose tissue can be obtained by conventional techniques known for the skilled person in the art (e.g., liposuction), from any suitable source of adipose tissue from any suitable animal, including mammals such as dogs, cats, horses, pigs, cows and humans. Preferably, pluripotent stem cells utilized in the present invention are derived from a mammal, such as from a human.

A convenient source of adipose tissue is from liposuction surgery. In fact, a large quantity of pluripotent cells can be obtained by simple aspiration from adipose tissue, for example, from lipoaspirate samples from aesthetic interventions. Because approximately 400,000 liposuction procedures are performed annually in the United States, this source of pluripotent cells, particularly "mesenchymal stem cells" (MSCs) is particularly promising for practicing the inventions disclosed herein.

In one instance, pluripotent cells of the invention are isolated from adipose tissue. The adipose tissue can be obtained from an animal, preferably a mammal by any suitable method. A first step in any such method requires the isolation of the adipose tissue from the source animal. The animal can be alive or dead, so long as adipose stromal cells within the animal are viable. Typically, human adipose tissue is obtained from a living donor, using well-recognized protocols such as surgical or suction lipectomy. The preferred method to obtain human adipose tissue is by excision or liposuction procedures well known in the art. The pluripotent cells of the invention are present in the initially excised or extracted adipose tissue, regardless of the method by which the adipose tissue is obtained.

From whatever source, the tissue source containing pluripotent cells is processed to separate the pluripotent cells of the invention from the remainder of the tissue. Pluripotent cells can be obtained by washing the tissue with a physiologically-compatible solution, such as phosphate buffer saline (PBS). Typically, a washing step consists of rinsing the adipose tissue with PBS, agitating the tissue, and allowing the tissue to settle. In addition to washing, the adipose tissue can be dissociated. Dissociation can occur by enzyme degradation (e.g., trypsin treatment). Alternatively, or in conjunction with such enzymatic treatment, other dissociation methods can be used such as mechanical agitation, sonic energy, or thermal energy. Cells are then centrifuged and the pellet (containing the pluripotent cells) is further treated after resuspension in an appropriate solution (e.g., PBS).

Pluripotent cells in the resuspended pellet can be separated from other cells of the resuspended pellet by methods that include, but are not limited to, cell sorting, size fractionation, granularity, density, molecularly, morphologically, and immunohistologically (e.g., by panning, using magnetic beads, FACS, MACS, or affinity chromatography.

In some immunologically-based methods of cell isolation, a pluripotent cell is obtained by positive selection, via the use of an antibody or other specific-binding protein, which binds to an epitope on the cell surface. For example, a sample comprising cells from adipose tissue from three genetically distinct subjects is contacted with an antibody that binds to a surface molecule (e.g., CD105, CD44, TERT or CD 29) so as to form a cell-antibody-complex, recovering the pluripotent cells; thereby obtaining isolated, non-culture expanded pluripotent cells. Upon forming an antigen-antibody complex, the antigen-antibody complexes are separated from the other subpopulations which are not bound to the antibody by a column, for example. Where the antibody is supported by a magnetic bead, a magnetic column can be used. The step of recovering the cells from the antibodies is performed by washes with suitable buffers, known to one skilled in the art. Alternately, pluripotent cells can be isolated by negative selection.

The presence of pluripotent cells may be verified by specific cell surface markers which are identified with unique monoclonal antibodies, for example, see U.S. Pat. No. 5,486,359. Pluripotent cells of the invention can proliferate and be induced to differentiate into cells of other lineages by conventional methods. Methods for identifying and subsequently isolating differentiated cells from their undifferentiated counterparts can be also carried out by methods well known in the art. See, e.g., Zheng et al. Rheumatology, 47:22-30 (2008). The capacity of the cells of the pluripotent cells of the invention to differentiate into one or more cell lineages can be assayed by conventional methods known by the skilled person in the art.

Pluripotent cells of the invention are also capable of being expanded in vitro. That is, after isolation, said cells can be maintained and allowed to proliferate in culture medium. Such medium is composed of any suitable cell medium, for example, Dulbecco's Modified Eagle's Medium (DMEM), with or without antibiotics, and glutamine, and/or supplemented with fetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include FBS, bovine serum (BS), calf serum (CS), fetal calf serum (FCS), newborn calf serum (NCS), goat serum (GS), horse serum (HS), porcine serum, donkey serum, sheep serum, rabbit serum, rat serum (RS), etc. Where cells are of human origin, supplementation of cell culture medium with a human serum, for example of autologous origin, can be used. Modulation of serum concentrations, withdrawal of serum from the culture medium can also be used to promote survival of one or more desired cell types. In another embodiment, pluripotent cells of the invention can be expanded in a culture medium of definite composition, in which the serum is replaced by a combination of serum albumin, serum transferrin, selenium, and recombinant proteins including but not limited to: insulin, platelet-derived growth factor (PDGF), and basic fibroblast growth factor (bFGF), as known in the art.

Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, and the like. Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin, ampicillin, gentamicin, bleomycin, hygromycin, kanamycin, mitomycin, etc. Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

The maintenance conditions of pluripotent cell population(s) of the invention can also contain cellular factors that allow cells to remain in an undifferentiated form. It is apparent to those skilled in the art that prior to differentiation supplements that inhibit cell differentiation must be removed from the culture medium. It is also apparent that not all cells require these factors and such factors may be incompatible with maintaining the pluripotent phenotype of the cells.

If desired, pluripotent cell population(s) can be clonally expanded using any suitable method for cloning cell populations. For example, a proliferated population of cells can be physically picked and seeded into a separate plate (or the well of a multi-well plate). Alternatively, the cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). The cells can be cloned by plating them at low density (e.g., in a Petri dish or other suitable substrate) and isolating them from other cells using devices such as a cloning rings. The production of a clonal population can be expanded in any suitable culture medium. In any event, the isolated cells can be cultured to a suitable point when their developmental phenotype can be assessed. In vitro expansion of pluripotent cells without inducing differentiation can be accomplished for example by using specially screened lots of suitable serum (such as fetal bovine serum or human serum).

Any of the steps and procedures for isolating pluripotent cells of the invention can be performed manually, for example by microscopic evaluation based on phenotype and/or marker expression. Alternatively, the process of isolating such cells can be facilitated and/or automated through one or more methods known in the art, for example, FACS or MACS sorting. For sorting and/or immunostaining of cells, an exemplary set of markers are shown in Table 1. Cells may be positive for one, two, three, four, five, six, seven, eight, nine, ten or more markers of interest. One of skill in the art will recognize that such markers are provided only as illustrations are not an exhaustive or limiting list of such markers or tissue/cell types. Additionally, pluripotent cells may be identified (e.g., by negative selection) for the absence of markers, including, but not limited to CD3, CD11b, CD14, CD19, CD31, CD34, CD45, CD62L, and HLA-DR.

TABLE 1

Non-limiting exemplary markers of select populations of pluripotent cells

| Cell Source | Markers |
| --- | --- |
| Adipose tissue/ umbilical cord perivascular cells | CD13, CD29, CD44, CD49e, CD 54, CD71, CD73, CD90, CD105, CD95L, CD105, CD117, CD166, SOX2, TERT |
| Endothelial tissue from umbilical cord vein/foreskin | CD34, CD36, CD105, CD150, CD151, CD160 |
| Endometrial cells | SOX2, TERT, CD29, CD105, CD117 |
| Chondrocyte-like cells | Collagen II, collagen X, aggrecan, ABCB1 (P-glycoprotein) |

Also provided herein are methods of doing business in which cells of the present invention are collected and provided. Tissues can be collected through any appropriate means, for example adipose tissue, foreskin and umbilical cord tissues can be collected by surgical or following birthing at a hospital or clinic. Tissues can be collected from multiple sites, including hospitals, clinics, physician's offices and tissue repositories. Thus, tissues from multiple genetically distinct individuals can be collected from the same source (e.g., hospital) as well as multiple different sources. In some instances, tissues which are the source of pluripotent cells can be transported to a central facility for combining, processing and/or extraction of pluripotent cells by any method known in the art, such as those described herein.

Methods for Extracting and Processing Adipose Tissue

In practicing the methods disclosed herein, the cells that are administered to a patient are obtained from adipose tissue. Adipose tissue can be obtained by any method known to a person of ordinary skill in the art. For example, adipose tissue may be removed from a patient by suction-assisted lipoplasty, ultrasound-assisted lipoplasty, and excisional lipectomy. In addition, the procedures may include a combination of such procedures, such as a combination of excisional lipectomy and suction-assisted lipoplasty. As the tissue or some fraction thereof is intended for reimplantation into a patient the adipose tissue should be collected in a manner that preserves the viability of the cellular component and that minimizes the likelihood of contamination of the tissue with potentially infectious organisms, such as bacteria and/or viruses. Thus, the tissue extraction should be performed in a sterile or aseptic manner to minimize contamination.

For suction-assisted lipoplastic procedures, adipose tissue can be collected by insertion of a cannula into or near an adipose tissue depot present in the patient followed by aspiration of the adipose into a suction device. In one embodiment, a small cannula may be coupled to a syringe, and the adipose tissue may be aspirated using manual force. Using a syringe or other similar device may be desirable to harvest relatively moderate amounts of adipose tissue (e.g., from 0.1 ml to several hundred milliliters of adipose tissue).

Suction assisted lipoplasty may be desirable to remove the adipose tissue from a patient as it provides a minimally invasive method of collecting tissue with minimal potential for stem cell damage. A suitable system includes a single-use disposable aspiration system, which allows extraction of adipose into sterile sealed bag for further processing. Preferably the system employs a relatively small device which has the advantage that the lipoaspiration can be performed with only local anesthesia, as opposed to general anesthesia.

The adipose tissue that is removed from a patient is collected into a sterile container for further processing. The device is designed for and dedicated to the purpose of collecting tissue for manufacture of a processed adipose tissue cell population, which includes stem cells and/or endothelial precursor cells. In some cases, the device is a single-use disposable aspiration system which extracts adipose tissue from a patient into a sterile sealed bag. In alternative embodiments, the device may be any conventional device that is typically used for tissue collection by physicians performing the extraction procedure.

The amount of tissue collected will be dependent on a number of variables including, but not limited to, the body mass index of the donor, the availability of accessible adipose tissue harvest sites, concomitant and pre-existing medications and conditions (such as anticoagulant therapy), and the clinical purpose for which the tissue is being collected. Moreover, the stem cell percentage of 100 ml of adipose tissue varies from individual to individual. For example the concentration of stem cells in tissue extracted from a lean individual is greater than that extracted from an obese donor). This reflects a dilutive effect of the increased fat content in the obese individual. During preparation of therapeutic compositions including the stem cells it is advantageous to quantify and characterize the extracted stem cell population in order to control the number of stem cells incorporated into the therapeutic composition and delivered to the patient.

The preferred method to obtain human adipose tissue is by excision or liposuction procedures well known in the art. The pluripotent cells of the invention are present in the initially excised or extracted adipose tissue, regardless of the method by which the adipose tissue is obtained. The adipose tissue is then processed to facilitate separation/concentration of the stem cells. For example, pluripotent cells can be obtained by washing the tissue with a physiologically-compatible solution, such as phosphate buffer saline (PBS). Typically, a washing step consists of rinsing the adipose tissue with PBS, agitating the tissue, and allowing the tissue to settle. In addition to washing, the adipose tissue can be dissociated. Dissociation can occur by enzyme degradation (e.g., trypsin treatment). Alternatively, or in conjunction with such enzymatic treatment, other dissociation methods can be used such as mechanical agitation, sonic energy, or thermal energy. Cells are then centrifuged and the pellet (containing the pluripotent cells) is further treated after resuspension in an appropriate solution (e.g., PBS).

Pluripotent cells in the resuspended pellet can be separated from other cells of the resuspended pellet by methods that include, but are not limited to, cell sorting, size fractionation, granularity, density, molecularly, morphologically, and immuno-histologically (e.g., by panning, using magnetic beads, FACS, MACS, or affinity chromatography. In some immunologically-based methods of cell isolation, a pluripotent cell is obtained by positive selection, via the use of an antibody or other specific-binding protein, which binds to an epitope on the cell surface. The step of recovering the cells from the antibodies is performed by washes with suitable buffers, known to one skilled in the art. Alternately, pluripotent cells can be isolated by negative selection. In the present invention, the kit includes sterile containers and/or reagents to facilitate the separation/concentration of the stem cells in the lipoaspirate. The presence of pluripotent cells is preferably assessed prior to reintroduction using, for example, specific cell surface markers and/or counting techniques. Such assessment allows quantification and characterization of the extracted stem cell population in order to control the number of stem cells incorporated into a therapeutic composition and delivered to the patient.

Phenotypic Alteration/Differentiation of Stem Cells

Pluripotent cells obtained using the system of the present invention can be reintroduced to the patient without expansion. However, in alternative embodiments, the pluripotent cells are optionally expanded in vitro. That is, after isolation, said cells can be maintained and allowed to proliferate in culture medium. It is within the skill of one in the art to modify or modulate concentrations of media and/or media supplements as necessary for the cells used. In another embodiment, pluripotent cells of the invention can be expanded in a culture medium of definite composition, in which the serum is replaced by a combination of serum albumin, serum transferrin, selenium, and recombinant proteins including but not limited to: insulin, platelet-derived growth factor (PDGF), and basic fibroblast growth factor (bFGF), as known in the art. The maintenance conditions of pluripotent cell population(s) of the invention can also contain cellular factors that allow cells to remain in an undifferentiated form where undifferentiated stem cells are desired.

Pluripotent cells obtained using the system of the present invention can be reintroduced to the patient without phenotypic alteration/differentiation. The pluripotent cells can alternatively be induced to phenotypically change into a desired cell type. Pluripotent cells can be directed to phenotypically change/differentiate into a desired cell type, e.g., a chondrocyte, or a cell with properties of a desired cell type, e.g., a chondrocyte-like cell (for example, a cell expressing collagen II, collagen X, aggrecan, ABCB1, or a combination of these). Such phenotypic changes are specific to the cell type to be produced as are the methods for directing differentiation.

Typically, one or more additional substances can be added to the culture to induce a desired phenotypic change. Such substances can include activators of intracellular signaling pathways (mitogen-activated protein kinases and Smads), activators of transcription factors (sox9, L-sox5, and L-sox6), activators of production and interaction with extracellular matrix proteins (collagen II, aggrecan, and cartilage oligomeric matrix protein), growth factors, cytokines, chemokines, hormones and environmental factors (oxygen tension). Non-limiting examples of substances which can induce a change to a chondrocyte-like cell include, but are not limited to dexamethasone, beta-glycerophosphate, ascorbic acid, transforming growth factor, and/or bis(bromomethyl)propanediol (BMP).

MSCs can also be cultured in a three-dimensional matrix to induce a desired phenotypic change. For example, production of chondrocyte-like cells from MSCs or other pluripotent cells can comprise a three-dimensional culture of MSCs utilizing a three-dimensional scaffold comprised of extracellular matrix. Multiple types of matrices can be used to support the pluripotent cells as they differentiate. One form of matrix is a polymeric mesh or sponge; another is a polymeric hydrogel. Typically, a matrix is biodegradable over a time period of less than a year. Such extracellular matrices can be composed of any suitable material, including collagen, albumin, and fibrin; and polysaccharides such as alginate and polymers of hyaluronic acid, polylactic acid (PLA), polyglycolic acid (PGA), and polylactic acid-glycolic acid (PLGA), polyorthoesters, polyanhydrides, polyphosphazenes, and combinations thereof.

Alternately, pluripotent cells can be cultured in a "micromass" culture comprising artificially conglomerated cells (e.g., by centrifuging a cell suspension to produce a pellet) which is substantially free of extracellular matrix. As used herein, "substantially free of extracellular matrix" means that a composition contains only a negligible amount of any exogenously added extracellular matrix, but may contain such materials produced by the cells.

Therapeutic Compositions of Stem Cells

For the administration in the prevention and/or treatment of a disorder, such as joint disorders (e.g., osteoarthritis), cells of the invention (e.g., chondrocyte-like cells derived from pluripotent cells) can be formulated in a suitable pharmaceutical composition, comprising cells of the invention, in a therapeutically or prophylactically effective amount, together with a suitable pharmaceutically acceptable vehicle. The pharmaceutical composition of the invention can contain a prophylactically or therapeutically effective amount of the cells of the invention, preferably in a substantially purified form, together with the suitable vehicle in the appropriate amount in order to provide the form for proper administration to the subject. One form of therapeutic composition includes stem cells encapsulated in hydrogel as part of a 3-dimensional platform as described below.

As used herein the term "prophylactically or therapeutically effective amount" refers to the amount of cells of the invention contained in the pharmaceutical composition which is capable of producing the desired therapeutic effect. One of skill in the art will recognize that cell numbers (e.g., dosage amount) will vary depending upon multiple factors including, but not limited to site of administration, extent of disease, and method of administration. For example, an administration directly into the joint of a subject suffering from OA will typically contain a smaller number of cells than an administration of the cells into the bloodstream. The dose of cells disclosed herein can be repeated, depending on the patient's condition and reaction, at time intervals of days, weeks or months as determined necessary by a treating physician or other healthcare professional. As previously described, assessment of the extracted stem cell population prior to incorporation into a pharmaceutical composition allows quantification and characterization of the extracted stem cell population in order to control the number of stem cells incorporated into a therapeutic composition thereby facilitating delivery of a desired prophylactically or therapeutically effective amount of stem cells to the patient.

The pharmaceutical composition of the invention can be formulated according to the chosen form of administration. For example, a pharmaceutical composition is prepared in a liquid dosage form, e.g., as a suspension, to be injected into the subject in need of treatment. Illustrative, non-limiting examples, include formulating the pharmaceutical composition of the invention in a sterile suspension with a pharmaceutically acceptable vehicle, such as saline solution, phosphate buffered saline solution (PBS), or any other suitable pharmaceutically acceptable carrier, for parenteral administration to a subject, e.g., a human being, preferably via intravenous, intraperitoneal, subcutaneous, etc., although further administration routes may be also possible.

If desired, the cells of the present invention can be purified, after induction of phenotypic alteration by use of antibody-mediated positive and/or negative cell selection in order to enrich the cell population. Phenotypically altered cells of the invention (e.g., chondrocyte-like cells) can be administered to a subject without further processing or additional procedures to further purify, modify, stimulate, or otherwise change the cells. Alternately, phenotypically altered cells can be purified (e.g., by positive selection) such that a composition comprising the cells (e.g., chondrocyte-like cells) is substantially free of pluripotent cells.

The term "pharmaceutically acceptable vehicle" refers to a composition approved by a regulatory agency of the Federal or a state government or listed in the U.S. Pharmacopeia, or European Pharmacopeia, or other generally recognized pharmacopeia for use in animals, including humans. The term "vehicle" refers to a diluent, adjuvant, excipient, or carrier with which the cells of the invention are administered, thus, the vehicle must be compatible with the cells. Examples of suitable pharmaceutical vehicles are described in "Remington's Pharmaceutical Sciences" by E. W. Martin. Illustrative, non-limiting, examples of vehicles for the administration of cells contained in a pharmaceutical composition of the invention include, for example, a sterile saline solution (0.9% NaCl), PBS, etc.

The pharmaceutical compositions of the invention, if desired, can also contain, when necessary, additives to enhance, control, or otherwise direct the intended therapeutic effect of the cells comprising said pharmaceutical composition, and/or auxiliary substances or pharmaceutically acceptable substances, such as minor amounts of pH buffering agents, tensioactives, co-solvents, preservatives, etc. Also, for stabilizing the cell suspension, it is possible to add metal chelating agents. The stability of the cells in the liquid medium of the pharmaceutical composition of the invention can be improved by means of adding additional substances, such as, for example, amino acids such as aspartic acid, glutamic acid, etc. Pharmaceutically acceptable substances that can be used in the pharmaceutical composition of the invention are known, in general, by the skilled person in the art and are normally used in the manufacture of cellular compositions.

In one example of a therapeutic composition, chondrocyte-like cells are produced from isolated pluripotent cells by any of the methods described herein. Chondrocyte-like cells are then prepared for application to subjects in need of the cells. Chondrocyte-like cells can also be prepared in pharmaceutical dosages (e.g., in a pharmaceutically acceptable solution) and stored in appropriate containers. The chondrocyte-like cells can be stored in an appropriate manner (e.g., frozen) until needed. Additionally, the pharmaceutical dosages can be placed in pre-prepared syringes, catheters or other medical devices appropriate for delivery to an affected joint. One of skill in the art will recognize that dosage amount, needle length and other such parameters can be adjusted for any individual preparation.

A pharmaceutical composition containing cells of the present invention may be stored until use by means of conventional methods known by the skilled person in the art. For short term storage (less than 6 hours) the pharmaceutical composition containing said cells may be stored at or below room temperature in a sealed container with or without supplementation with a nutrient solution. Medium term storage (less than 48 hours) is preferably performed at 2-8° C., the pharmaceutical composition comprising an iso-osmotic, buffered solution in a container composed of or coated with a material that prevents cell adhesion. Longer term storage is preferably performed by appropriate cryopreservation and storage under conditions that promote retention of cellular function.

Cells in either prepared dosages or pre-dosage containers can be shipped to medical facilities through any approved delivery system (governmentally approved and/or commercial). Cells can be delivered directly from the manufacturer or via an intermediary. Fees can be collected for delivery of the cells through any appropriate means (e.g., credit card, credit account, cash, check, etc.).

Encapsulation of Stem Cells—3D Platform

In an embodiment of the invention, a 3-dimensional (3D) platform is created to support cells introduced as a therapeutic composition into the body. In general terms the platform is created by extraction of SVM with or without purification of stem cells. The cells are dispersed in a biocompatible gel/polymeric matrix. Preferably the gel is biocompatible and biodegradable, for example a fibrin hydrogel. The gel containing the stem cells is then formed into microbeads thereby increasing the active surface area of the therapeutic composition. The formation of the microbeads can be performed manually or mechanically. Preferably, the microbeads are of 10 to 50 µL in size and each bead includes from 2,000 to 10,000 stem cells. The concentration of stem cells in the microbeads is selected so as to be high enough to achieve the desired therapeutic effect without reduced the effectiveness of the encapsulation and viability of the stem cells. A suitable concentration of stem cells has been found to be 200 stem cells per µL. This concentration of stem cells has been found to promote maintenance and viability of the stem cells within the microbeads for up to 14 days. The therapeutic composition of microbeads of gel containing stem cells can then be injected or applied superficially as a therapeutic composition or to augment autologous adipose tissue transplant procedures.

The 3D platform provides significant advantages compared to a dispersed suspension of stem cells. For example, the stem cells remain in groups, keeping on interaction, normal proliferation and gross factor secretion whereas in suspension, the single stem cells are unable to sustain normal development in form of single cells in suspension. Additionally, the 3D platform defends the encapsulated stem cells against environmental changes and mechanical stress upon delivery of the stem cells into the hosting tissue. The 3D matrix supports the stem cells assuring normal metabolism over an extended period as compared to a suspension of stem cells. The support of the stem cells by the 3D platform also enhances the storage or cryostorage of the stem cells facilitating maintenance, transport and delivery of stem cells at the time and place required for a procedure. Additionally, the initial amount of available and injected cells can be determined during preparation of the 3D platform, which allows development of dose-dependent controlled treatment. This is facilitated, as described above, by characterization of the stem cell population prior to and/or during preparation of the therapeutic composition.

The advantages of the 3D platform provide significant therapeutic benefits. The encapsulated stem cells in the 3D platform can be more accurately delivered to a precise location in the human body and will remain in the targeted location—as opposed to stem cells in suspension which rapidly dissipate from the injection site. Moreover, as described above, the 3D platform increases the longevity and functionality of the stem cells by protecting them against chemical and mechanical stress at the injection site. Maintaining the stem cells in the target location and extending their viability extends the treatment effects of the stem cells thereby enhancing the treatment and or reducing the need for repetition of the treatment.

In a preferred embodiment adipose-derived stem cells are encapsulated in the 3D platform to generate a therapeutic composition. Preparation of encapsulated stem cells requires three general steps. First, stem cells must be extracted, and isolated. The extraction and isolation of stem cells can be performed using conventional methods and/or the methods described herein. Second, the stem cells are mixed with a liquid phase biocompatible pro-polymer. Third, the mixture is caused to gel by crosslinking of the pro-polymer to form a polymer. As result, the stem cells are embedded in polymeric biodegradable hydrogel network which serves as 3D culture and support system for the stem cells. A range of biocompatible polymers are know to those of skill in the art including, for example, fibrin, alginate and collagen polymers. A suitable polymer is biocompatible and biodegradable but provides suitable mechanical and chemical support to the stem cells during a period over which they can have therapeutic effect. In a preferred embodiment, a Fibrin/thrombin gel is used suitable for maintaining the stem cells for a period of three to fourteen days.

A therapeutic composition comprising encapsulated stem cells can be introduced into tissues adjacent the site of an injury. Because the cells are encapsulated they do not migrate away from the site of introduction. However, the stem cells can proliferate in vivo. Moreover, the presence of the encapsulated stem cells can stimulate growth/proliferation of tissues adjacent the encapsulated stem cells by, for example, the release of cytokines, growth factors and anti-inflammatory factors. It is thought that encapsulated stem cells introduced in this manner can achieve regenerative healing without differentiation and integration of the stem cells actually introduced. Indeed, in some embodiments, encapsulation of the stem cells extends the period of the treatment effect by maintaining the stem cells in undifferentiated form isolated from factors in the tissue which might engender differentiation of the stem cells. Thus, in some embodiments it is desirable to introduce the stem cells adjacent the site of an injury rather than directly at the site of an injury.

Administration of Therapeutic Compositions

The administration of the pharmaceutical composition of the invention to the subject in need thereof can be carried out by conventional means. In a particular embodiment, said pharmaceutical composition can be administered to the subject in need by intravenous administration using devices such as syringes, catheters, trocars, cannulae, etc. In any case, the pharmaceutical composition of the invention will be administrated using the appropriate equipments, apparatus, and devices which are known by the skilled person in art in a therapeutically or prophylactically effective amount, together with a suitable pharmaceutically acceptable vehicle.

Cells disclosed herein can be applied by several routes including systemic administration by venous or arterial infusion (including retrograde flow infusion) or by direct injection into the affected anatomical site. A pharmaceutical composition containing the cells may be injected in a single bolus, through a slow infusion, or through a staggered series of applications separated by several hours, several days or weeks. In any case, the pharmaceutical composition of the invention will be administrated to the target tissue using the appropriate equipments, apparatus, and devices which are known by the skilled person in art in a therapeutically or prophylactically effective amount. In alternative embodiments, the 3D platform can be utilized to augment fat autografts implanted using conventional techniques.

One of skill in the art will recognize that cell numbers (e.g., dosage amount) will vary depending upon multiple factors including, but not limited to site of administration, extent of disease, and method of administration. For example, an administration directly into the joint of a subject suffering from OA will typically contain a smaller number of cells than an administration of the cells into the bloodstream. The dose of cells disclosed herein can be repeated, depending on the patient's condition and reaction, at time intervals of days, weeks or months as determined necessary by a treating physician or other healthcare professional.

In a preferred embodiment, stem cells are encapsulated as part of a 3D platform as described above. The 3D platform incorporating the stem cells are then delivered to a target location to achieve the desired therapeutic effect. The 3D platform can be administered to the subject in need by direct administration into target tissue using devices such as syringes, catheters, trocars, cannulae, etc. In a preferred embodiment the 3D platform is administered percutaneously under image guidance to a desired location.

One mode of treatment introduces stem cells encapsulated in the 3D platform adjacent tissues to be treated. The 3D platform maintains the stem cells in their undifferentiated from and protects the stem cells from chemical and mechanical stress at the site of introduction. The encapsulated stem cells are able to survive and/or proliferate in vivo for an extended period as compared to stem cells in suspension. The encapsulated stem cells release cytokines, growth factors, anti-inflammatory factors which migrate out of the 3D platform into the surrounding tissues. These factors engender a therapeutic effect in the target tissues adjacent the site of injection of the 3D platform.

In one example, a 3D platform encapsulating stem cells is used to treat osteoarthritis. Rather than injecting a suspension of stem cells directly into a joint, the 3D platform is introduced sub-chondrally using an image-guided needle or similar technology. The stem cells in the 3D platform do not themselves differentiate into tissues to repair the joint. However cellular factors released from the 3D platform are able to migrate into the osteo-arthritic tissues of the joint rejuvenating the tissues and thereby stimulate those tissues to repair themselves. Essentially the 3D platform permits the release of factors from the encapsulated stem cells with reduce inflammation and trigger self repair in the affected tissues of the joint such as the damaged cartilage. Triggering self-repair of the tissues allows for creation of defect repairs which more closely approximate the natural tissue. This is advantageous to direct injection of stem cells to differentiate into repair tissue because such approach generally results in tissues that do not have the desired structural features of the natural tissues.

Cells and pharmaceutical compositions of the present disclosure can be used in a combination therapy with other substances useful for treating the same disorder. Such combination therapy can comprise the cells of the present invention directly combined with other substances (e.g., other pharmaceuticals), or in conjunction with other substances. Combination therapy can also include delivery of therapeutic compositions as described herein along with Autologous/Allogeneic Origin of Stem Cells The cells disclosed herein can be cells of autologous or allogeneic origin. Autologous stem cells are derived from the individual into whom the stem cells are later reinfused. Autologous stem cells are advantageous in that, being the individuals own tissue, they do not engender an immune response from the recipient. Allogeneic stem cells on the other hand, are derived from one or more individuals other than the recipient. These stem cells can illicit an immune/rejection response in some circumstances. Steps can be taken to reduce the chance of rejection, such as by using tissue-matched donors. Allogeneic stem cells can still be utilized in certain applications. Although autologous stem cells are preferred, allogeneic stem cells can, for example be utilized as part of a 3D-platform described above—the allogeneic stem cells are effective to deliver therapeutic cellular factors for a period after introduction to the patient and are protected from rejection by the 3D platform at least for the limited period during which they have their therapeutic effect.

Where cells of allogeneic origin are to be used, for example, extracted adipose tissue from two or more genetically distinct individuals is combined prior to isolation of pluripotent cells from the tissue. The term "genetically distinct" as used herein, indicates that at least one difference at the genomic level exists between subjects or donors. Adipose tissue can be collected from 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more subjects or donors. In some instances, cells for use in treating a subject (e.g., chondrocyte-like cells) are derived from pluripotent cells donated from two or more genetically diverse subjects. For example, MSCs from adipose tissue collected from liposuction performed on different individuals can be pooled prior to culturing under conditions which lead to chondrocyte-like cell production. Alternately, cells from a single individual may be induced to phenotypically switch to chondrocyte-like cells and then combined. Such an approach allows for immediate treatment of individuals suffering from joint disorders such as osteoarthritis by using "off the shelf" cells. Without being bound by theory, such an approach can be utilized due to the relative lack of immune surveillance at the site of insertion (e.g., the synovial space). If desired, the cells of the present invention can be purified, after induction of phenotypic alteration by use of antibody-mediated positive and/or negative cell selection in order to enrich the cell population. Phenotypically altered cells of the invention (e.g., chondrocyte-like cells) can be administered to a subject without further processing or additional procedures to further purify, modify, stimulate, or otherwise change the cells. Alternately, phenotypically altered cells can be purified (e.g., by positive selection) such that a composition comprising the cells (e.g., chondrocyte-like cells) is substantially free of pluripotent cells.

Using the methods and compositions provided herein the present disclosure provides other methods which can be used to provide therapeutic cells (e.g., chondrocyte-like cells) to a plurality of patients. For instance, therapeutic cells can be produced in large batches comprising cells derived from multiple genetically distinct donors (e.g., from multiple liposuction patients). Liposuction (or lipectomy) is a common procedure in the United States, with approximately 400,000 such procedures performed each year. Cells from such procedures can be procured from multiple locations and multiple genetically-distinct individuals. As described above, pluripotent cells from such sources can be isolated to produce the therapeutic cells described herein in large numbers (e.g., millions, billions, trillions).

As therapeutic cells provided to an individual in need thereof can be allogeneic with respect to the recipient (e.g., patient suffering from osteoporosis), the methods described herein provide therapeutic cell populations which can be produced on a large scale. In some instances, cells sufficient to treat 10, 50, 100, 200, 300, 400, 500, 600, 700, 800, 900, 1000, 5000, 10,000, 20,000, 50,000, 100,000, 500,000, 1,000,000, 10,000,000, 50,000,000, 100,000,000 or more subjects can be produced. Therapeutic cells can be produced in large quantities and divided into smaller populations for distribution. Smaller divisions can include packaging into individual treatment packages (e.g., a pre-loaded syringe), or other appropriate sized forms (e.g., canisters containing sufficient cells for multiple treatments). Therapeutic cells can be produced prior to an individual patient's need (e.g., days, weeks, or months prior to such need) or can be produced in response to an individual patient's need.

For example, a sample comprising cells from adipose tissue from several genetically distinct donors is combined with antibodies, which are directed to the surface of other subpopulation(s) which exist in the sample (e.g., CD11b, CD14, CD19), thereby trapping the non-pluripotent cells. One of skill in the art will recognize that such selection of cells can be performed prior to culturing cells, following cell culture, or both. Thus, in some embodiments, pluripotent cells from one or more genetically distinct individuals may be substantially free of non-pluripotent cells. Furthermore, pluripotent cells from multiple individuals can be collected and/or combined prior to culturing, following culturing, or both. Thus, pluripotent cells from 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more individuals can be combined.

EXAMPLES

Example 1: Isolation and Culture of Adipose Derived Pluripotent (Stem) Cells

In this example, pluripotent cells are isolated from human adipose tissue. Adipose tissue is collected from multiple anonymous donors during surgical procedures, such as liposuction. The tissue is minced into pieces ranging from 1-2 mm$^3$, washed with phosphate-buffered saline (PBS) and digested with 1.5 mg collagenase type I per mg of adipose tissue for 60 minutes at 37° C. Cells are subjected to multiple centrifugations and floating cells are removed. The cell mixture is exposed to erythrocyte lysis buffer, incubated at room temperature for 10 minutes, and centrifuged at 300×g for 10 minutes. The supernatant is removed. Collected cells are grown for 3-4 generations in DMEM+10% FBS at 37° C.

Approximately $10^7$ cells are transferred to a 15 mL polypropylene conical tube, centrifuged at 300×g for 10 minutes and the supernatant is aspirated. To enrich the population for pluripotent cells the resulting pellet is resuspended in 80 μL PBS. FcR blocking buffer and anti-CD105 antibody conjugated with allophycocyanin (APC) is added to the cell suspension according to manufacturer's instructions. The suspension is mixed well and incubated at 2-8° C. for 10 minutes. One ml PBS is added and cells are centrifuged at 300×g for 10 minutes and the supernatant is aspirated. Cells are resuspended in 70 μL PBS. 10 μL FcR blocking reagent and 10 μL Anti-APC MicroBeads (Miltenyi Biotec) are added to the suspension. Cells are incubated at 2-8° C. for 15 minutes. Cells are washed by adding 1 ml PBS and centrifuged at 300×g for 10 minutes and the supernatant is aspirated. Cells are resuspended in 500 μl PBS. Cells are then run through an autoMACS Column (Miltenyi Biotec) according to manufacturer's instructions. CD105 positive cells are cultured in Proliferation Medium for 3-5 days at 37° C.

Example 2: Harvesting and Differentiation of Pluripotent Cells

In this example, CD105-positive cells are harvested from culture and differentiated into chondrocyte-like cells. Cultured CD105-positive cells prepared as described in Example 1 are collected from culture and washed by adding 2 ml PBS to the tissue culture flask and aspirating the supernatant. One ml trypsin/EDTA (0.05%/0.53 mM) is added to cover the cells and the mixture is incubated at 37° C. for 5-10 minutes. Dissociation of cultured cells is examined under a microscope. Gentle tapping of the flask or increased incubation time may be necessary to facilitate further dissociation as needed. Five ml pre-warmed proliferation medium is added to the flask upon sufficient dissociation and the cells are resuspended by pipetting and transferred to a 15 ml polypropylene conical tube. The flask is washed with an additional 5 ml proliferation medium, which is also transferred to the conical tube to collect all cells. Cells are centrifuged at room temperature at 300 g for 10 minutes. The supernatant is removed and the cells are gently resuspended in 0.5 ml proliferation medium. Cell number and viability is determined by exposing 10 μL cells to Trypan Blue and using a hemocytometer. Cells are then diluted to a final concentration of $3 \times 10^5$ cells/ml in the expansion medium.

To cause the CD105-positive cells to differentiate into chondrocyte-like cells, the following protocol is One ml of the cell suspension is transferred to a 15 ml polypropylene conical tube and centrifuged for 5 minutes at 150 g at room temperature. The supernatant is aspirated and 1 ml pre-warmed Differentiation Medium (20 ml DMEM+10% FBS with 2 ml growth factor cocktail (10 μl/ml beta-TGF1, 5 μl/ml bis(bromomethyl)propanediol, and 0.1 μl/ml dexamethasone). Cells are centrifuged for 5 minutes at 150 g at room temperature and the supernatant is aspirated. 1 ml pre-warmed Differentiation Medium is added, but the cells are not suspended. The tube is incubated upright at 37° C. with 5% CO2, 95% N2 and >95% humidity. Fresh Differentiation Medium is added every third day, being careful not to disturb the cell pellet. After 28 days, the nodules (micromass culture) have matured and can be frozen and stored or transferred to a recipient.

Example 3: Determination of Chondrocyte-Like Phenotype

In this example, cells prepared as detailed in Examples 1 and 2 are examined to determine whether they have differentiated into chondrocyte-like cells. Formalin is diluted with PBS to a final concentration of 3.7% (neutral buffered formalin or "NBF"), ethanol is diluted with deionized water to concentrations as needed. Roti-Plast (paraffin) is heated at 58° C. until melted.

Differentiation Medium is aspirated from a micromass culture prepared as described in Example 2 and is washed once with 1 ml PBS. The micromass is fixed by immersion in NBF (the micromass or nodule is freely suspended in NBF) for 6-12 hours at room temperature with gentle agitation. Nodules are placed in an embedding cassette with filter paper and dehydrated by applying ethanol as follows: 2×30 min in 70% ethanol, 2×30 min in 80% ethanol, 2×30 min in 90% ethanol, and 2×30 min in 100% ethanol. The embedding cassette is then incubated in Roti-Histol (xylol substitute—Roth). Nodules are then removed from the embedding cassette and embedded with preheated Roti-Plast in a Bio-mold and cooled at −20° C. overnight.

Five gm thick tissue sections are prepared using a microtome and the sections are transferred to a 40° C. water bath. Tissue sections are placed on HistoBond slides, incubated at 52° C. for 3 hours and then cooled to room temperature before staining or storage. Sections to be analyzed are deparaffinized using 2×5 min in Roti-Histol, 2×5 min in 100% ethanol, 2×5 min in 96% ethanol, 2×5 min in 80% ethanol and 2×5 min in 70% ethanol. Sections are rinsed twice in deionized water and twice in 5 mm PBS. Sections are then incubated in permeabilization buffer (PBS with 1% BSA, 10% normal donkey serum and 0.3% Triton X-100) for 45 min at room temperature. The permeabilized section is then dabbed dry and encircled using a hydrophobic pen. Mouse anti-human aggrecan antibody (10 µg/ml) in PBS with 1% BSA and 10% normal donkey serum is then applied (150 µL) and incubated overnight at 2-8° C. in a humidified chamber. Sections are washed with washing buffer (PBS+ 1% BSA) three times for five minutes. 150 µl donkey anti-mouse IgG conjugated with rhodamine (diluted 1:50 in washing buffer) is added and incubated at room temperature for 1 hour in the dark. The secondary antibody is removed by tilting the slide and gently removing by blotting. 150 µL DAPI (diluted 1:1000 in washing buffer) is added to each section and incubated in the dark for 15 minutes. Sections are then washed twice with washing buffer in the dark and rinsed once with deionized water. Sections are examined using a fluorescent microscope for positive signals indicating the presence of aggrecan, and thus a phenotypic shift to chondrocyte-like cells.

Example 4: Treatment of Osteoarthritis by Injection of Chondrocyte-Like Cells In this example, treatment of osteoarthritis is performed by injecting chondrocyte-like cells derived from adipose tissue pluripotent cells. Nodules of chondrocyte-like cells developed as described above are treated with EDTA, EGTA or enzymatic digestion (e.g., trypsin) and resuspended. Cell suspensions are then injected into an affected knee or elbow joint.

The administration of the chondrocyte-like cells can be carried out by conventional means. In a particular embodiment, chondrocyte-like cells can be administered into the joint of subject in need using devices such as syringes, catheters, trocars, cannulae, etc. The administration can be performed percutaneously/arthroscopically and can be repeated as necessary to achieve the desired therapeutic effects. In any case, the pharmaceutical composition of the invention will be administrated using the appropriate equipments, apparatus, and devices which are known by the skilled person in art in a therapeutically or prophylactically effective amount, together with a suitable pharmaceutically acceptable vehicle.

Example 5: 3D Platform—Encapsulated Stem-Cells

In this example adipose-derived stem cells are encapsulated in a three-dimensional gel to form a 3D platform prior to introduction into a patient. Treatment with encapsulated stem cells provides significant biologic advantage over treatment with a dispersed suspension of stem cells. For example, the stem cells remain in groups, keeping on interaction, normal proliferation and gross factor secretion whereas in suspension, the single stem cells are unable to sustain normal development in form of single cells in suspension. Additionally, the matrix of the 3D platform defends the encapsulated stem cells against environmental changes and mechanical stress upon delivery of the stem cells into the hosting tissue. The matrix of the 3D platform supports the stem cells assuring normal metabolism. Advantageously, in the present example, the initial amount of available and injected cells is known to patient and physician, which allows development of dose-dependent controlled treatment.

Preparation of encapsulated stem cells requires three general steps. First, stem cells must be extracted, and isolated. The extraction and isolation of stem cells can be performed using conventional methods and/or the methods described herein. Second, the stem cells are mixed with a liquid phase biocompatible pro-polymer. Third, the mixture is caused to gel by crosslinking of the pro-polymer to form a polymer. As result, the stem cells are embedded in polymeric biodegradable hydrogel network which serves as 3D culture and support system for the stem cells.

In one embodiment, stem cells are derived from adipose tissue as follows. Adipose tissue is collected from a patient by mini liposuction into a sterile syringe in amount of 50-100 ml in a doctor's office. The extracted adipose tissue in the sterile syringes is processed on site or transported to a nearby facility for processing. The contents of the sterile syringes is then released into sterile 50 ml tubes and spun in a centrifuge at 200 g for 5 min. After centrifugation, the fraction of white fat is removed. The cell fraction is weighed and Liberase (Roche) is added in final concentration 12 mg/ml (0.28 Wunsch/ml). The cell fraction is digested with Liberase for 30 minutes in 36.6° C. in hot air shaker. At the end of 30 minutes the digestion is halted by addition of DMEM medium supplemented 15% human plasmanate (commercial). The treated cell fraction is the washed twice with reconstituted "StemPro"—a non-animal source recombinant medium (Invitrogen). The pellet containing the cell fraction is then plated in 75 cm$^2$ flask and incubated overnight in 5.5% CO2 incubator at 36.6° C. After overnight incubation cells are removed by exposition to "TrypLE Select"—recombinant trypsin (Invitrogen) for 8 min followed by washing in reconstituted StemPro medium. After washing, the stem cells are resuspended in 1 ml of StemPro medium. The suspension of stem cells can be characterized at this point by counting the cells using, e.g., a Scepter automated cell counter. A 100 µL sample of the suspension is removed for flow cytometry cell characterization and microbiology testing.

The remaining 900 µL of the stem cell suspension is used for encapsulation as follows. A 5 ml solution of Fibrinogen is prepared in concentration 10 mg/ml in tris-based DPBS.2. Stem cells in suspension are added to the solution of Fibrinogen to achieve final concentration of 200,000 cells/ml by gentle pipetting. The amount of stem cell solution to be added can be calculated because the stem cell solution has previously been characterized/counted. The mixture of the fibrinogen precursor and stem cells is the pipetted into 10 ml of thrombin solution in concentration 50 mg/ml. The resulting mixture is incubated in 5.5% CO2 at 36.6° C. for thirty minutes to form a gel including the encapsulated stem cells.

In a preferred embodiment the gel is formed into microbeads by manual or using an automatic chip device. The microbeads are preferably 10-50 µL in size. The microbeads are designed and the stem cell concentrated selected such the microbeads can support and maintain the stem cells in vivo for a period of 3 to 14 days during which period the stem cells remain within the microbead and release therapeutic factors into the surrounding tissues. The microbeads are kept in incubator until 2 hrs before scheduled procedure. At that point the product is delivered to Surgical Center at ambient temperature. Alternatively, the encapsulated stem cells are frozen and delivered in ready-to-use condition. Microbeads can be frozen by slow freezing or vitrification method and delivered in ready-to-use condition. Alternatively, the stem cells can be extracted and the 3-D platform and microbeads can be created at the site of the procedure using appropriate devices.

Example 6: Treatment of Osteoarthritis Utilizing 3D Platform

In this example, treatment of osteoarthritis is performed by injecting encapsulated stem cells in the form of the 3D platform. The 3D platform is created as described above utilizing a fibrin gel encapsulating adipose-derived autologous stem cells. (Note that in alternative embodiments stem cells of other types-and origin can be utilized). The 3D platform microbeads incorporating the stem cells are then injected sub-chondrally adjacent damaged tissues such as damaged cartilage of an affected knee or elbow joint.

The administration of the 3D platform can be carried out by conventional means. In a particular embodiment, the 3D platform is introduced sub-chondrally using devices such as syringes, catheters, trocars, cannulae, etc. The administration can be performed percutaneously/arthroscopically and can be repeated as necessary to achieve the desired therapeutic effects. For example, the 3D platform is introduced sub-chondrally using an image-guided needle or similar technology. In any case, the pharmaceutical composition of the invention will be administrated using the appropriate equipments, apparatus, and devices which are known by the skilled person in art in a therapeutically or prophylactically effective amount.

The microbeads maintain the stem cells in the target location in undifferentiated from and protect the stem cells from chemical and mechanical stress at the site of introduction. The encapsulated stem cells are able to survive and/or proliferate in vivo within the microbeads for an extended period as compared to stem cells in suspension introduced into the joint. In a preferred embodiment the encapsulated stem cells are maintained for 3-14 days. The encapsulated stem cells release cytokines, growth factors, anti-inflammatory factors which migrate out of the 3D platform into the surrounding tissues. These factors engender a therapeutic effect in the target tissues adjacent the site of injection of the 3D platform. The cellular factors released from the 3D platform are able to migrate into the osteo-arthritic tissues of the joint rejuvenating the damaged tissues and thereby stimulating those tissues to repair themselves and achieve a therapeutic result. At the end of the 3-14 days the fibrin of the microbeads is digested and the stem cells are no longer maintained. The procedure can be repeated as necessary to achieve the desired therapeutic effect.

Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages or features will be embodied in any particular embodiment of the present invention. Additional advantages and aspects of the present invention are apparent in the following detailed description and claims.

A number of publications and patents have been cited hereinabove. Each of the cited publications and patents are hereby incorporated by reference in their entireties. All publications, patents and patent applications are herein incorporated by reference in their entirety to the same extent as if each individual publication, patent or patent application was specifically and individually indicated to be incorporated by reference in its entirety.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

The invention claimed is:

1. A method for treating a patient comprising:
   (a) receiving a therapeutic composition comprising an injectable suspension of a plurality of microbeads of a biocompatible hydrogel,
      wherein each microbead comprises from about 2,000 to about 10,000 adipose-derived stem cells encapsulated within the hydrogel; and
      wherein the microbeads are adapted to release cellular factors from the stem cells to a target tissue of the patient into which the microbeads are introduced;
   (b) introducing said therapeutic composition adjacent a diseased or injured tissue in the patient; and
   (c) causing the release of therapeutic cellular factors from said stem cells encapsulated within the hydrogel to said diseased or injured tissue.

2. The method of claim 1, wherein the therapeutic composition is introduced sub-chondrally adjacent a diseased or injured tissue in the patient.

3. The method of claim 1, wherein the diseased or injured tissue is the result of a joint disorder.

4. The method of claim 1, wherein the diseased or injured tissue is the result of osteoarthritis.

5. The method of claim 1, wherein the microbeads have a volume between 10 and 50 µL.

6. The method of claim 1, wherein the microbeads comprise about 200 stem cells per microliter.

7. The method of claim 1, wherein the microbeads are adapted to protect the stem cells from mechanical and chemical stress when introduced to the patient.

8. The method of claim 1, wherein the microbeads are adapted to maintain the stem cells in an undifferentiated condition for a period of three to fourteen days.

9. The method of claim 1, wherein the stem cells are autologous stem cells.

10. The method of claim 1, wherein the stem cells are allogeneic stem cells.

11. The method of claim 1, wherein the plurality of microbeads are frozen microbeads.

12. The method of claim 1, wherein the plurality of microbeads are thawed microbeads adapted to be resuspended in a biocompatible fluid before injection into a patient.

13. The method of claim 1, wherein the stem cells are mesenchymal stem cells.

14. The method of claim 1, wherein the stem cells are uncultured stem cells.

15. The method of claim 1, wherein the microbeads are formed from about 10 mg/mL fibrinogen in the presence of about 50 mg/mL thrombin.

* * * * *